United States Patent [19]

Towfigh

[11] Patent Number: 4,608,046

[45] Date of Patent: Aug. 26, 1986

[54] FLAT FOLDED FEMALE URINARY AID

[76] Inventor: Keivan Towfigh, 51 Harvard Ave., Medford, Mass. 02155

[21] Appl. No.: 752,351

[22] Filed: Jul. 3, 1985

Related U.S. Application Data

[63] Continuation of Ser. No. 143,831, Apr. 25, 1980, abandoned, which is a continuation of Ser. No. 825,939, Aug. 19, 1977, abandoned.

[51] Int. Cl.⁴ .............................................. A61F 5/44
[52] U.S. Cl. ...................................... 604/329; 4/144.3
[58] Field of Search ........................... 604/329–331; 4/144.1–144.4; 229/53, 93; 128/294, 295; 239/24, 33; 138/173; 428/134, 155; D24/57

[56] References Cited

U.S. PATENT DOCUMENTS

| | | | |
|---|---|---|---|
| D. 196,473 | 10/1963 | Hill | D83/1 |
| 347,416 | 8/1886 | Buckingham | 229/93 |
| 754,948 | 3/1904 | White | 229/93 UX |
| 1,171,431 | 2/1916 | Gorton | 229/53 |
| 1,407,872 | 2/1922 | Lacey | 4/144.4 |
| 1,510,973 | 10/1924 | Behan | 128/295 |
| 2,490,969 | 12/1949 | Kinyon | 4/110 |
| 2,878,486 | 3/1959 | Bartlett et al. | 4/110 |
| 2,937,645 | 5/1960 | Sachs | 128/295 |
| 3,000,015 | 10/1924 | Hart | 4/110 |
| 3,072,125 | 1/1963 | O'Brien | 128/295 |
| 3,335,714 | 8/1967 | Glesy | 128/2 |
| 3,432,866 | 3/1969 | Schwartz | 4/110 |
| 3,512,185 | 5/1970 | Ellis | 4/110 |
| 3,613,122 | 10/1971 | Gross et al. | 4/110 |
| 3,776,235 | 12/1973 | Ratcliffe et al. | 128/295 |
| 3,864,759 | 2/1975 | Horiuchi | 4/110 |
| 4,023,216 | 5/1977 | Li | 128/295 |

Primary Examiner—John D. Yasko
Assistant Examiner—J. L. Kruter
Attorney, Agent, or Firm—Wolf, Greenfield & Sacks

[57] ABSTRACT

A urinary aid for use by females includes a flat-folded tube having an end insertable between the labia. The tube is expandable by light hand squeezing to open the inserted end of the tube to a urine-receptive configuration which spread the labia and in which the device may be pressed against the uninary meatus. In one non-reuseable embodiment of the invention, the tube is provided with a thin coating which is temporarily water resistant but which is degradable. In another embodiment of the invention, the device is reuseable. In all embodiments, the device may be considered as disposable because of its low cost of manufacture. The device may be manufacutred using simple and economical manufacturing procedures.

5 Claims, 13 Drawing Figures

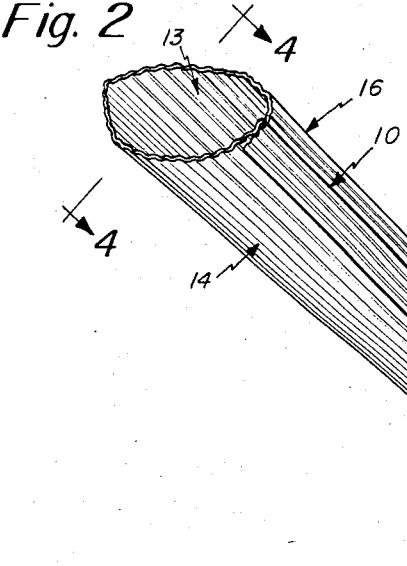
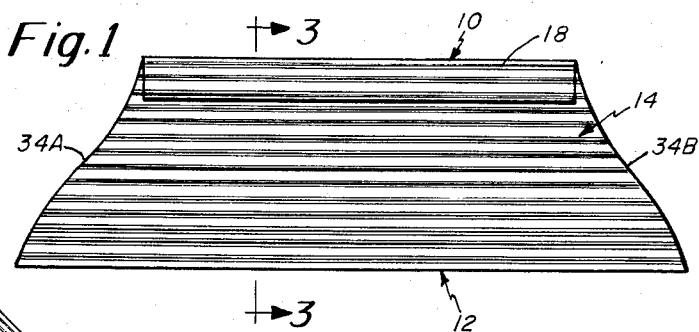
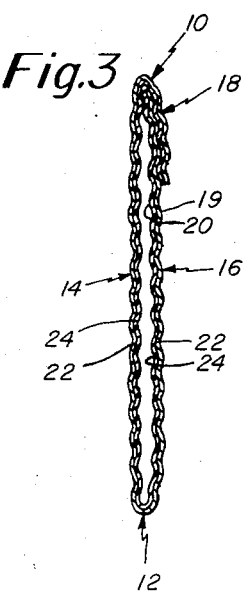
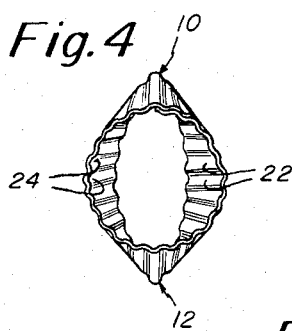
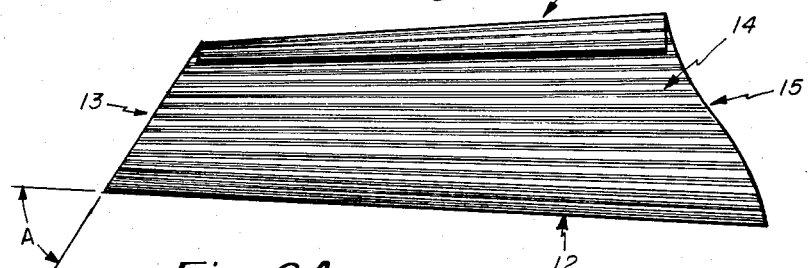
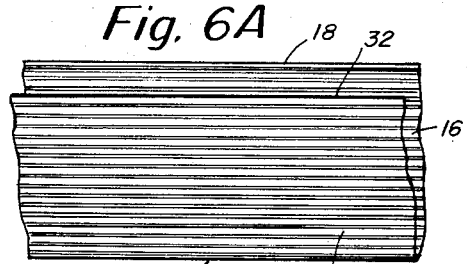
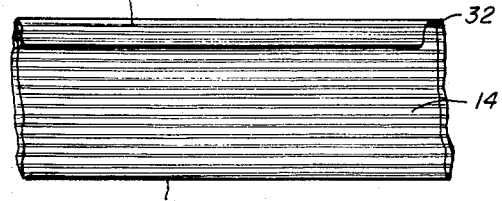
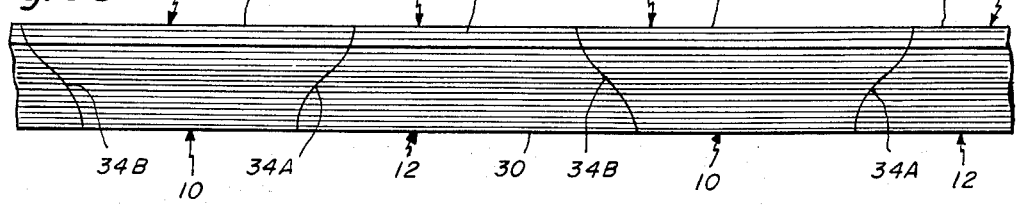

FLAT FOLDED FEMALE URINARY AID

This application is a continuation of application Ser. No. 143,831, filed 4/25/80 now abandoned which is a continuation of 825,939 filed 8/19/77 now abandoned.

BACKGROUND OF THE INVENTION

This invention relates to improvements in feminine hygenic devices and, particularly to devices to facilitate urination by females in circumstances where toilet facilities are unavailable or, if available are unsanitary or otherwise undesirable. The desirability for a urinating aid for use by females, by which they may urinate with the same facility as a male, has been recognized for some time and numerous devices and aids have been proposed in the prior art. Notwithstanding the desirability for such a device, not all of the devices proposed in the prior art have suffered from serious difficulties. For example, many are bulky, uncomfrotable and awkward to use. Most have been relatively expensive to manufacture and are not readily disposable or degradable. Others tend to result in dripping and perhaps soiling the user's clothes.

It is among the general objects of the invention to provide an improved urinating aid which avoids the foregoing and other difficulties.

SUMMARY OF THE INVENTION

In accordance with the present invention, the device is in the form of a tubular member which is flat-folded. In one embodiment of the invention, the tubular member is formed from paper having a relatively low wet strength in which the interior surface of the tubular member preferably is coated with a very thin film of urine or water-resistant material which will resist becoming flacid at least for a time interval of the order of one to two minutes and which will thereafter become limp and degradable upon continued exposure to water or other moisture. The tube is formed from sheet stock having a plurality of corrugations which define alternating ridges and grooves extending parallel to the general longitudinal axis of the device. In another, reuseable, embodiment of the invention, the tubular member may be formed from a thin sheet of plastic material. In each embodiment, the ends of the device are cut to a shape such that either end may be inserted against the urinary meatus. In use, an end of the flat-folded device is inserted between the labia and against the urinary meatus. The inserted tube then is manually squeezed to cause the inserted end to expand, thus parting the labia and forming an enlarged urine-receptive opening. One or both ends of the device may be frayed or rolled to provide a soft, or at least unsharp insertion surface.

It is among the objects of the invention to provide a urinary aid for females by which they may urinate in a standing position.

Another object of the invention is to provide a urinary aid for females which is drip-free.

A further object of the invention is to provide a urinary aid for females which minimizes turbulent flow and, thereby, minimizes dripping.

Another object of the invention is to provide a device of the type described which may be easily carried or readily dispensed from a commercial vending device.

A further object of the invention is to provide a device of the type described which is disposable and easily degradable.

A further object of the invention is to provide a device of the type described which does not require awkward or uncomfortable manipulations.

A further object of the invention is to provide a device of the type described which is very simple and inexpensive to manufacture.

Another object of the invention is to provide a device of the type described in which the inlet end of the device may be easily modified and varied in shape by the user to assure a proper seal between the device and the seal.

DESCRIPTION OF THE DRAWINGS

The foregoing and other objects and advantages of the invention will be appreciated more fully from the following further description thereof, with reference to the accompanying drawings wherein:

FIG. 1 is a plan view of one embodiment of the device as seen in a flat-folded configuration;

FIG. 2 is a perspective illustration of the device shown in FIG. 1 illustrating the manner in which it is expanded into a useable configuration;

FIG. 3 is an end view of the flat-folded device shown in FIG. 1;

FIG. 4 is an end view of the device in its useable configuration as seen from what may be considered as the inlet end thereof;

FIG. 5 is a side elevation of the device when in its opened, useable configuration, as would be seen from the right of FIG. 4;

FIG. 6A is an illustration of a step in the manufacture of the device in which an elongate strip is first folded;

FIG. 6B is an illustration of the next successive folding step in which a marginal flap portion is folded and adhered to define a flat tube;

FIG. 6C is an illustration of the manner in which the flat tube shown in 6B may be cut to form a succession of devices;

DESCRIPTION OF THE PREFERRED EMBODIMENT

Figure 7:
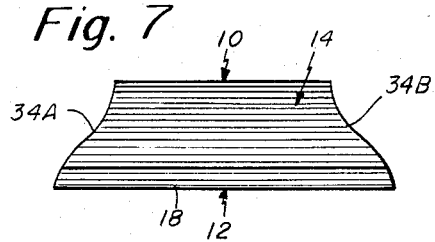
FIG. 7 is an illustration similar to FIG. 1 showing a device, cut from the flat tube shown in FIG. 6C but with the flap disposed along the bottom fold line.

FIG. 1 shows a non-reuseable embodiment of the device in its flat-folded configuration and FIG. 2 illustrates it in an expanded configuration, as it might be during use. As shown in FIGS. 1 and 3, the device is in the form of a flat-folded tubular member, folded at what may be considered to be generally parallel top and bottom fold lines 10, 12 which define the side panels 14, 16. In this embodiment, the width of the device, as measured between the fold lines 10, 12 is uniform along the length of the device. The device may be made from sheet material which is corrugated, folded and cut, as will be described, and which is secured in its generally tubular form by a flap 18 which extends from one of the side panels over the other side panel and is glued to the other side panel. The flat-folded article shown in FIGS. 1 and 3 may be packaged in that flat configuration in accordance with any of a variety of conventional packing techniques and the article thus packaged takes up little space and lends itself to machine vending from a variety of conventional vending machines, should it be desired to make such devices available in public toilet facilities. The flat-folded configuration also is easily carried in a pocket or handbag.

In use, one of the ends of the folded device is inserted between the user's labia, toward and against the urinary meatus. During or just after insertion in the folded configuration, the user compresses the device, adjacent the inserted end, by lightly squeezing the fold lines 10, 12 together. This causes the side walls 14, 16 particularly at the inserted end, to expand to define an enlarged urine-receptive opening (for example, at 13 in FIG. 2) which may be pressed lightly but firmly against the urinary meatus to receive urine from the urethral opening in readiness for discharge. As illustrated in FIGS. 2 and 4, the configuration of the device at this time is such that the cross-sectional configuration of the passage within the device, from the inlet 13 end to the outlet end 15, will change progressively from a somewhat elliptical or circular to a more oblate oval or elliptical configuration. Although the progressively changing configuration is not strictly essential because of the corrugations, described below, it is noted that the V-shaped passage which would be defined at the bottom fold 12 of the funnel-like passage does tend to promote more streamlined emission of the urine stream from the device with reduced splashing or dripping tendencies. As mentioned, however, it is not critical that the device be compressed to define the progressively changing cross-sectional shape and it will operate satisfactorily if the manner in which it is compressed results in a substantially regular elliptical cross-section throughout the length of the device.

As mentioned, a non-reuseable embodiment of the device may be formed from a degradable, fibrous material such as thin paper 19 having a low wet strength of the order of between 0.005 and 0.050 inches thickness. Preferably, the inner surface of the device is coated with a film 20 of plastic or starch material which is substantially impermeable and resistant to water at least for a few minutes which, in most instances, will be sufficient for the urination procedure to have been completed. By way of example only, the inner surface may be coated with plastic film such as polyethylene of a thickness of the order of 0.001 to 0.005 inches. Should starch be used as a coating, the thickness of the film 20 may be greater.

The flexible sheet material from which the device is made is preferably embossed or otherwise corrugated to define the alternating ridges 22 and grooves 24 which extend substantially parallel (at least before distortion to the useable shape) and longitudinally of the device. As mentioned, the grooves 24 tend to minimize turbulence and promote the emission of urine in a substantially laminar and continuous stream, thus minimizing the tendency to drip or splash, which is undesirable. The ridges and grooves also facilitate smooth and uniform bending of the panels 14, 16 from their flat-folded to a near circular configuration. From the foregoing, it should be appreciated that the device can be used entirely in one-handed operation.

The ends of the device preferably are formed so that an end may be expanded to a more circular, inlet-defining configuration, it will define, approximately, a generally circular or elliptical shape which lies in or nearly in a plane extending at an angle of less than 90° (preferably about 45°) to the longitudinal axis of the device. Whether the device is actually expanded to this configuration in use will depend on whether the user compresses the inlet end to that extent. This is illustrated at the angle A in FIG. 5. This enables the device to be inserted in a manner which will facilitate direction of the urine stream forwardly and away from the user. It may be noted, however, that it is not strictly essential that the end of the device used as an inlet be distorted to assume the circular configuration described and that, depending on the extent to which the fold lines 10, 12 are urged together, the configuration of the inlet opening may be controlled by the user as she may desire. Preferably, both ends of the embodiment described thus far are formed in the same manner so that either end may be used as the inlet or outlet. In the embodiments shown, the opposite inlet and outlet ends of the panels extend generally along directions which will tend to converge so that when both ends are expanded from their flat-folded configuration, the approximate planes defined by the end openings will both be disposed at an angle to the longitudinal dimension of the device. In the preferred embodiment, the ends are cut to form somewhat of a shallow S-shaped configuration (see FIG. 1) which may be sinusoidal and tends to result in the approximately planar inlet opening 13 (described above).

In the embodiment illustrated in FIGS. 1-5, the ends are cut along lines which are disposed substantially symmetrically about the middle of the tube. This provides significant manufacturing advantages and economies because the device thus is provided with symmetrical ends, either of which can be used as an inlet. In a preferred mode of manufacture, illustrated in FIG. 6, the coated, embossed paper is in the form of an elongate strip 26 which may be supplied from a roll (not shown). The strip may be folded and glued by conventional straight line, untimed folding and gluing machinery. For example, a first longitudinal fold 30 may be made slightly off center from the longitudinal center line of the strip to define the side panels 14, 16 and from an overextending marginal portion 18 which projects beyond the edge 32 of the opposite panel. The marginal portion 18 then may be folded over and adhered to and against the adjacent margin of the opposite panel to form the strip into a continuous flat tube. The continuous flat tube then may be cut alternately with S-shaped cuts, as suggested at 34A, 34B in FIG. 6C to sever a succession of devices from the tube.

It will be appreciated that each successive device cut from the flat tubular strip will be of a reversed configuration in that the flap 18 defined by the folded-over marginal portion will, in one device, extend along the upper fold line 10 (as shown in FIGS. 1-5), while the next successive device cut from the flat tubular strip will have its marginal flap 18 extending along what has been described as the bottom fold line 12. FIG. 7 illustrates a flat-folded device having its flap 18 extending along the bottom fold 12. Each type of device operates satisfactorily. From the foregoing, it will be appreciated that the manufacturing technique is extremely simple and inexpensive and results in no waste of material.

Figure 8:
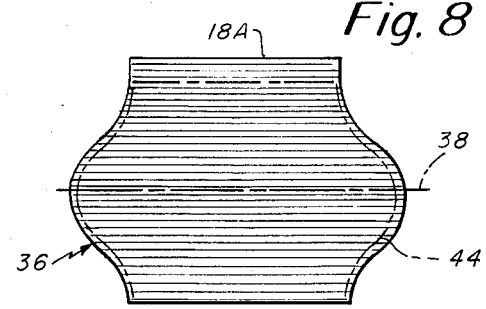
FIG. 8 is an illustration of a die cut blank from which an individual device may be made in accordance with an alternate mode of manufacture.

It may be noted that the device may be manufactured by other techniques, for example, by stamping out individual pieces 36 in a pattern suggested in FIG. 8 although that is considered to be a more expensive procedure. Should this latter technique be utilized, it might be noted that the blank is substantially symmetrical along a longitudinal center line 38 except for the provision of a marginal glue strip blank 18A extending along one side edge of the blank.

Figure 9:
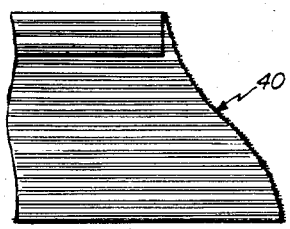
FIG. 9 is an illustration of an end portion of a device in accordance with the invention, having a softened cut edge.
Figure 10:
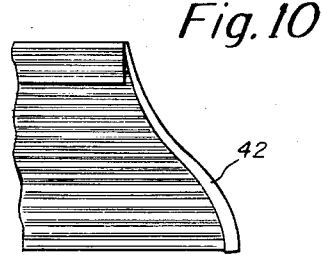
FIG. 10 is an illustration of an end of a device having a folded over or rolled configuration.
Figure 11:
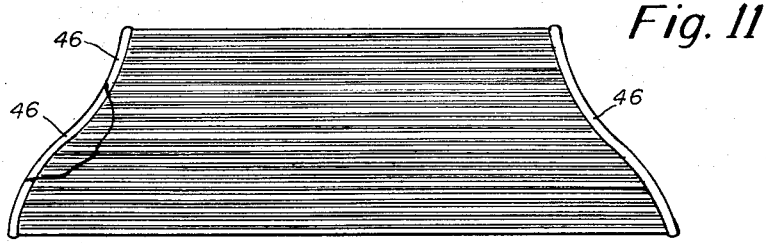
FIG. 11 is an illustration of a once-piece, reuseable, molded plastic embodiment of the device.

Depending on the nature of the specific material from which the device is made, it may be desirable to soften the cut edges at the inlet and/or outlet ends of the device. This may be desirable, for example, where the device is made from a paper which might tend to present a somewhat sharp edge where it is cut. The cut edges may be softened by a variety of techniques, for example, by lightly abrading or fraying the cut edges, as suggested at 40 in FIG. 9. The roughening of the edges may be accomplished by any of a variety of suitable roughening tools (such as sandpaper) which will tend to disrupt and raise the paper fibers along the cut edge. Alternatively, the device may be formed to define a rolled-rim indicated at 42 in FIG. 10. The rolled rim 42 may be formed by forming a small slit at the ends of the fold lines and then folding over the end portions of the side panels. Alternatively, when the device is made from a stamped blank (FIG. 8), the ends may be prefolded, as suggested by the phantom line 44 in FIG. 8, thus defining the smooth, rolled edge, before the blank is folded to its flat-folded configuration FIG. 11 shows another embodiment of the invention which is similarly disposable but which may be reused. In this embodiment, the device is formed in its entirety from a water-resistant material which will not become limp. For example, it may be formed from a thermoplastic material which can be extruded continuously in a flat tube and then cut. The ends of each cut device then may be heated slightly to eliminate any sharpness at the ends of the device and, if desired, to form a bead 46 about the opening. Alternatively, the device shown in FIG. 11 may be formed by injection molding.

Thus, I have described an improved urinary aid for females which avoids the difficulties which have been presented by the prior art devices. In particular, the device is inexpensive to manufacture, is simple to use, without mess and is disposable. Moreover, it enables the user to effect a good, firm and comfortable seal with simple and effective manipulation thus enhancing its sanitary use. It may be used rapidly under any conditions and does not require substantial disrobing. Moreover it has a variable contour inlet opening which may be controlled by the extent to which the device is squeezed which further promotes the ability of the device to provide an effective mess-free seal during use.

It should be understood that the foregoing description of the invention is intended merely to be illustrative thereof and that other embodiments and modifications may be apparent to those skilled in the art without departing from its spirit.

Having thus described the invention, what I desire to claim and secure by Letters Patent is:

1. A urinary aid for feminine use comprising:

a flat-folded tubular member having a pair of flexible side panels defined by a pair of parallel fold lines which extend longitudinally of the tubular member, each end of the tubular member terminating in an openable end, said panels being expandable from a flat-folded configuration to an opening-defining configuration in response to compression of the fold lines toward each other, as least one of the openable ends of the tubular member being dimensioned so as to be insertable, in its flat-folded configuration, between the user's labia and being constructed and arranged so as to part the labia in response to said compression;

the ends of the side panels, at least at one end of said member, being of a configuration such that when said end is expanded to its opening-defining configuration, said end will define an opening which extends generally along a plane which is disposed at an angle to the longitudinal dimension of the member;

said ends of said panels being S-shaped.

2. A urinary aid as defined in claim 1 wherein each of said ends is of said configuration and wherein the planes defined at said ends are non-parallel to each other.

3. A urinary aid as defined in claim 1 wherein said angle is of the order of about 45°.

4. A urinary aid as defined in claim 1 wherein each of said fold lines defines a V-shaped channel interiorly of the member.

5. A method for facilitating urination by a female comprising:

providing a flat-folded tubular member having a pair of flexible side panels defined by a pair of parallel fold lines which extend longitudinally of the tubular member, each end of the tubular member terminating in an openable end, said panels being expandable from a flat-folded configuration to an opening-defining configuration in response to compression of the fold lines toward each other, at least one of the openable ends of the tubular member being dimensioned so as to be insertable, in its flat-folded configuration, between the user's labia and being constructed and arranged so as to part the labia in response to said compression;

inserting said at least one openable end of the tubular member, in a flat-folded configuration, between the user's labia and while so inserted, compressing the fold lines of the tubular member to cause the panels to expand from the flat-folded configuration to an opening-defining configuration while simultaneously causing the labia to part in response to said compression and expansion;

urging the tubular member while in its opening-defining configuration into firm engagement with the meatus surrounding the user's urethral opening thereby providing a seal about the urethral opening and enabling a stream of urine to be directed away from the user upon urination.

* * * * *